US009957339B2

(12) United States Patent
Thackeray et al.

(10) Patent No.: US 9,957,339 B2
(45) Date of Patent: *May 1, 2018

(54) COPOLYMER AND ASSOCIATED LAYERED ARTICLE, AND DEVICE-FORMING METHOD

(71) Applicants: The University of Queensland, St. Lucia (AU); Rohm and Haas Electronic Materials LLC, Marlborough, MA (US)

(72) Inventors: James W. Thackeray, Braintree, MA (US); Ke Du, Queensland (AU); Peter Trefonas, III, Medway, MA (US); Idriss Blakey, Clayfield (AU); Andrew Keith Whittaker, Toowong (AU)

(73) Assignees: ROHM AND HAAS ELECTRONIC MATERIALS LLC, Marlborough, MA (US); THE UNIVERSITY OF QUEENSLAND, St. Lucia (AU)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/820,699

(22) Filed: Aug. 7, 2015

(65) Prior Publication Data

US 2017/0037171 A1    Feb. 9, 2017

(51) Int. Cl.
*C08F 220/28* (2006.01)
*B05D 1/00* (2006.01)
*G03F 7/20* (2006.01)
*G03F 7/09* (2006.01)

(52) U.S. Cl.
CPC ............ *C08F 220/28* (2013.01); *B05D 1/005* (2013.01); *G03F 7/094* (2013.01); *G03F 7/20* (2013.01); *C08F 2220/281* (2013.01); *C08F 2438/03* (2013.01)

(58) Field of Classification Search
CPC .......... C08F 2220/286; C08F 2220/287; C08F 2220/288; G03F 7/91; G03F 7/094; G03F 7/20; B05D 1/005
See application file for complete search history.

(56) References Cited

U.S. PATENT DOCUMENTS

| | | |
|---|---|---|
| 2,760,863 A | 8/1956 | Plambeck, Jr. |
| 2,850,445 A | 9/1958 | Oster |
| 2,875,047 A | 2/1959 | Oster |
| 3,097,096 A | 7/1963 | Oster |
| 3,427,161 A | 2/1969 | Laridon et al. |
| 3,479,185 A | 11/1969 | Chambers, Jr. |
| 3,549,367 A | 12/1970 | Chang et al. |
| 4,343,885 A | 8/1982 | Reardon, Jr. |
| 4,442,197 A | 4/1984 | Crivello et al. |
| 4,603,101 A | 7/1986 | Crivello |
| 4,624,912 A | 11/1986 | Zweifel et al. |
| 7,666,572 B2 | 2/2010 | Harada et al. |
| 8,431,325 B2 | 4/2013 | Hashimoto et al. |
| 8,618,217 B2 | 12/2013 | Kanna |
| 8,846,303 B2 | 9/2014 | Hatakeyama et al. |
| 8,846,838 B2 | 9/2014 | Matsumiya et al. |
| 8,883,400 B2 | 11/2014 | Wang et al. |
| 8,945,808 B2 | 2/2015 | David et al. |
| 2007/0231713 A1 | 10/2007 | Bristol |
| 2007/0231751 A1 | 10/2007 | Bristol et al. |
| 2008/0038676 A1 | 2/2008 | Li et al. |
| 2008/0193879 A1 | 8/2008 | Allen et al. |
| 2008/0311530 A1 | 12/2008 | Allen et al. |
| 2009/0087799 A1* | 4/2009 | Tachibana ............... G03F 7/091 430/323 |
| 2010/0173245 A1 | 7/2010 | Wang et al. |
| 2011/0245395 A1 | 10/2011 | Komoriya et al. |
| 2012/0021355 A1 | 1/2012 | Kim et al. |
| 2012/0328983 A1 | 12/2012 | Kramer |
| 2013/0059252 A1 | 3/2013 | Maruyama et al. |
| 2013/0071789 A1 | 3/2013 | Iwashita et al. |
| 2013/0115553 A1 | 5/2013 | Wang |
| 2013/0143162 A1* | 6/2013 | Hatakeyama ............. G03F 7/11 430/296 |
| 2013/0337379 A1* | 12/2013 | Yao ........................... G03F 7/40 430/271.1 |
| 2014/0199617 A1 | 7/2014 | Tsubaki et al. |
| 2014/0370442 A1 | 12/2014 | Ober et al. |
| 2015/0140484 A1 | 5/2015 | Takizawa et al. |
| 2015/0177613 A1 | 6/2015 | Jain et al. |
| 2017/0037178 A1 | 2/2017 | Thackeray et al. |

FOREIGN PATENT DOCUMENTS

| | | |
|---|---|---|
| JP | 2014174329 A | 9/2014 |
| JP | 2015-120852 A | 7/2015 |

(Continued)

OTHER PUBLICATIONS

English translation of WO 2012/081863 a2 obtained Dec. 12, 2016 from WIPO Patentscope and translated with Google, 9 pages.*
Fujitani et al, OBPL for the Best Solution to Resist Outgassing and Out-of-Band Issues in EUVL toward 1Xnm Proc. of SPIE, vol. 9048 (2014) 90482H-1-90482H-7.
Hagiwara et al.; "Surface Segregation Analysis of Hydrophobic Additive of Non-topcoat Resist"; Journal of Photopolymer Science and Technology; vol. 21; No. 5; 2008; pp. 647-654.
Kim et al.; "CD uniformity imporvement for EUV resists process: EUV resolution enhancement layer"; Samsung Electronics, Co. Ltd., Semiconductor R&D Center, Process Devel. Team; 2011; http://proceedings.spiedigitallibrary.org on Apr. 23, 2015, Proc. of SPIE vol. 7969, pp. 7966916-1 to 796916-10, year 2011.

(Continued)

*Primary Examiner* — Cynthia Hamilton
(74) *Attorney, Agent, or Firm* — Cantor Colburn LLP

(57) ABSTRACT

A copolymer is prepared by the polymerization of monomers that include an ultraviolet absorbing monomer, and a base-solubility-enhancing monomer. The copolymer is useful for forming a topcoat layer for electron beam and extreme ultraviolet lithographies. Also described are a layered article including the topcoat layer, and an associated method of forming an electronic device.

8 Claims, 6 Drawing Sheets

(56) References Cited

FOREIGN PATENT DOCUMENTS

| WO | 2012081863 A2 | 6/2012 |
| WO | 2013036555 A1 | 3/2013 |

OTHER PUBLICATIONS

Ohmori et al., "Progress of Topcoat and Resist Development for 193nm Immersion Lithography" Proc. of SPIE vol. (2006) 61531X-1-61531X-8.

Onishi et al., "The Novel Top-Coat Material for RLS Trade-off Reduction in EUVL" Proc. Of SPIE vol. 8322, (2012) 83222D-1-83222D-6.

Otake et al.; "Hydrophobic Surface Construction by Phase-Separation of Fluorinated Block Copolymer for Immersion Lithography"; Journal of Photopolymer Science and Technology; vol. 21; No. 5; 2008; pp. 679-684.

Sheehan et al.; "RAFT Technology for the Production of Advanced Photoresist Polymers"; E.I. DuPont de Nemours, Central Research and Development; 2008; 14 pages.

Solid surface energy data (SFE) for common polymers; Nov. 20, 2007, http://www.surface-tension.de/solid-surface-energy.html [Apr. 30, 2015 12:03:34 PM]; 2 pages.

Gabor, et al., Proc. SPIE vol.. 2724, Advances in Resist Technology and Processing XIII, 410-417, Jun. 14, 1996; doi:10.1117/12.241839.

Non-Final Office Action dated Jan. 30, 2017; U.S. Appl. No. 14/820,647, filed Aug. 7, 2015 (34 pages).

* cited by examiner

COPOLYMER AND ASSOCIATED LAYERED ARTICLE, AND DEVICE-FORMING METHOD

FIELD

The present invention relates to a copolymer, a photolithographic topcoat layer containing the copolymer, a layered article comprising the topcoat layer, and a method of forming an electronic device wherein the method utilizes the topcoat layer.

INTRODUCTION

Extreme ultraviolet (EUV) lithography and electron-beam lithography are promising technologies for patterning at scales of 20 nanometers and less. Sources of EUV radiation also produce longer wavelength radiation so-called out-of-band (OOB) radiation that can significantly deteriorate imaging performance. There is therefore a need for compositions that can reduce the negative impact of out-of-band radiation without unduly compromising other photolithographic responses. Co-filed U.S. patent application Ser. No. 14/820,647 describes a photoresist composition comprising a self-segregating OOB radiation-absorbing block polymer. For circumstances in which it is desirable to avoid or minimize modification of the photoresist composition, the present application describes a copolymer useful in an OOB radiation-absorbing, developer-soluble topcoat layer.

SUMMARY

One embodiment is a copolymer, wherein the copolymer comprises the polymerization product of monomers comprising: an out-of-band absorbing monomer; and a base-solubility-enhancing monomer; wherein a film cast from the copolymer has an extinction coefficient, k, of 0.1 to 0.5 at a wavelength in the range of 150 to 400 nanometers.

Another embodiment is method of forming a polymer layer, comprising spin-coating a polymer solution comprising 0.1 to 3 weight percent of the copolymer in a solvent selected from the group consisting of 2-methyl-2-butanol, 2-methyl-2-pentanol, combinations of 2-methyl-2-butanol and 2-methyl-2-pentanol, combinations of dipropylene glycol monomethyl ether and 2-methyl-2-butanol containing at least 90 weight percent 2-methyl-2-butanol, combinations of dipropylene glycol monomethyl ether and 2-methyl-2-pentanol containing at least 90 weight percent 2-methyl-2-pentanol, and combinations of dipropylene glycol monomethyl ether and 2-methyl-2-butanol and 2-methyl-2-pentanol containing at least 90 weight percent total of 2-methyl-2-butanol and 2-methyl-2-pentanol.

Another embodiment is a layered article comprising: a substrate; a photoresist layer over the substrate; and a topcoat layer comprising the copolymer, over and in contact with the photoresist layer.

Another embodiment is a method of forming an electronic device, comprising: (a) applying a photoresist layer onto a substrate; (b) applying a topcoat layer comprising the copolymer onto the photoresist layer; (c) pattern-wise exposing the photoresist layer through the topcoat layer to activating radiation; and (d) developing the exposed photoresist layer to provide a resist relief image.

These and other embodiments are described in detailed below.

BRIEF DESCRIPTION OF THE DRAWINGS

FIG. 5B a topcoat layer.

FIG. 10B photoresist CBP-4+ at 53 $\mu$C/cm$^2$; FIG. 10C photoresist CBP-4 at 55 $\mu$C/cm$^2$; FIG. 10D photoresist CBP-4+topcoat at 51 $\mu$C/cm$^2$; FIG. 10E photoresist CBP-4+ topcoat at 57 $\mu$C/cm$^2$; FIG. 10F photoresist CBP-4+ topcoat at 60 $\mu$C/cm$^2$.

DETAILED DESCRIPTION

Figure 1:
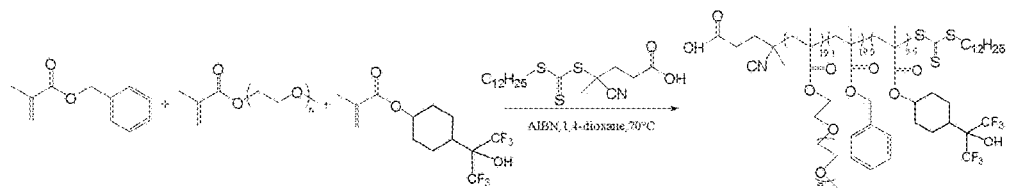
FIG. 1 is a reaction scheme for the synthesis of poly(PEGMA-co-BzMA-co-HFACHOH).

The present inventors have determined that a specific copolymer is useful as the primary or sole component of a topcoat layer for electron beam or extreme ultraviolet lithography. The copolymer absorbs out-of-band (OOB) radiation and readily dissolves in alkaline developer.

As used herein, the term "copolymer" includes random copolymers (including statistical copolymers), block copolymers, and graft copolymers. The random copolymers can include two, three, four, or more different types of repeat units. The block copolymers can be multiblock copolymers and can include, for example, diblock copolymers, triblock copolymers, tetrablock copolymers, or copolymers having five or more blocks. The blocks can be part of a linear copolymer, a branched copolymer where the branches are grafted onto a backbone (these copolymers are also sometimes called "comb copolymers"), a star copolymer (sometimes called a radial block copolymer), and the like. In graft copolymers, the compositions of the main chain and the one or more side chains are different either in composition or in the sequence of repeat units.

As used herein, the term "(meth)acrylate" means acrylate or methacrylate.

As used herein, the term "hydrocarbyl", whether used by itself, or as a prefix, suffix, or fragment of another term, refers to a residue that contains only carbon and hydrogen unless it is specifically identified as "substituted hydrocarbyl". The hydrocarbyl residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. When the hydrocarbyl residue is described as substituted, it can contain heteroatoms in addition to carbon and hydrogen.

Except where otherwise specified, the term "substituted" means including at least one substituent such as a halogen (i.e., F, Cl, Br, I), hydroxyl, amino, thiol, carboxyl, carboxylate, ester (including acrylates, methacrylates, and lactones), amide, nitrile, sulfide, disulfide, nitro, $C_{1-18}$ alkyl, $C_{1-18}$ alkenyl (including norbornenyl and adamantyl), $C_{1-18}$ alkoxyl, $C_{2-18}$ alkenoxyl (including vinyl ether), $C_{6-18}$ aryl, $C_{6-18}$ aryloxyl, $C_{7-18}$ alkylaryl, or $C_{7-18}$ alkylaryloxyl.

As used herein, the term "fluorinated" shall be understood to mean having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as —$CF_3$, —$C_2F_5$, —$C_3F_7$, or —$C_4F_9$).

As used herein, the term "alkyl" includes linear alkyl, branched alkyl, cyclic alkyl, and alkyl groups combining two-way and three-way combinations of linear, branched, and cyclic groups. The alkyl groups can be unsubstituted or substituted. Specific examples of alkyl groups include methyl, ethyl, 1-propyl, 2-propyl, cyclopropyl, 1-butyl, 2-butyl, 2-methyl-1-propyl, tertiary-butyl, cyclobutyl, 1-methylcyclopropyl, 2-methylcyclopropyl, 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl (neopentyl), cyclopentyl, 1-methylcyclobutyl, 2-methylcyclobutyl, 3-methylcyclobutyl, 1,2-dimethylcyclopropyl, 2,2-dimethylcyclopropyl, 2,3-dimethylcyclopropyl, 1-hexyl, 2-hexyl, 3-hexyl, 2-methyl-1-pentyl, 3-methyl-1-pentyl, 4-methyl-1-pentyl, 2-methyl-2-pentyl, 4-methyl-2-pentyl, 2-methyl-3-pentyl, 3-methyl-2-pentyl, 3-methyl-3-pentyl, 2,2-dimethyl-1-butyl, 3,3-dimethyl-1-butyl, 3,3-dimethyl-2-butyl, 2,3-dimethyl-1-butyl, 2,3-dimethyl-2-butyl, 1,2,2-trimethylcyclopropyl, 2,2,3-trimethylcyclopropyl, (1,2-dimethylcyclopropyl)methyl, (2,2-dimethylcyclopropyl)methyl, 1,2,3-trimethylcyclopropyl, (2,3-dimethylcyclopropyl) methyl, 2,2-dimethylcyclobutyl, 2,3-dimethylcyclobutyl, (1-methylcyclobutyl)methyl, 1,2-dimethylcyclobutyl, 2,3-dimethylcyclobutyl, (2-methylcyclobutyl)methyl, 1,3-dimethylcyclobutyl, 2,4-dimethylcyclobutyl, (3-methylcyclobutyl)methyl, 1-methylcyclopentyl, 2-methylcyclopentyl, cyclopentylmethyl, cyclohexyl, 1-norbornyl, 2-norbornyl, 3-norbornyl, 1-adamantyl, 2-adamantyl, octahydro-1-pentalenyl, octahydro-2-pentalenyl, octahydro-3-pentalenyl, octahydro-1-phenyl-1-pentalenyl, octahydro-2-phenyl-2-pentalenyl, octahydro-1-phenyl-3-pentalenyl, octahydro-2-phenyl-3-pentalenyl, decahydro-1-naphthyl, decahydro-2-naphthyl, decahydro-3-naphthyl, decahydro-1-phenyl-1-naphthyl, decahydro-2-phenyl-2-naphthyl, decahydro-1-phenyl-3-naphthyl, and decahydro-2-phenyl-3-naphthyl.

One embodiment is a copolymer, wherein the copolymer comprises the polymerization product of monomers comprising: an out-of-band absorbing monomer; and a base-solubility-enhancing monomer; wherein a film cast from the copolymer has an extinction coefficient, k, of 0.1 to 0.5 at a wavelength in the range of 150 to 400 nanometers.

As used herein, the term "out-of-band absorbing monomer" means a monomer that absorbs radiation at longer wavelengths than the radiation intended to expose the photoresist. For example, if the exposure device uses extreme ultraviolet radiation at a wavelength of 13.5 nanometers, then a monomer that absorbs ultraviolet radiation in the wavelength range 150 to 400 nanometers, specifically 190 to 300 nanometers, would be an out-of-band absorbing monomer. The "out-of-band absorbing monomer" provides the copolymer with absorbance in the range 150 to 400 nanometers. Specifically, a film cast from the copolymer has an extinction coefficient, k, of 0.1 to 0.5 at a wavelength (i.e., at least one wavelength) in the range of 150 to 400 nanometers. In some embodiments, the maximum value of the extinction coefficient, k, in the range 150 to 400 nanometers, is 0.1 to 0.5. It will be understood that the extinction coefficient, k, can be less than 0.1 and even zero at some wavelengths in the range 150 to 400 nanometers. The out-of-band absorbing monomer excludes fluorine-substituted ester groups. In some embodiments, the out-of-band absorbing monomer comprises an unsubstituted or substituted $C_6$-$C_{18}$ aryl group that is free of fluorine, an unsubstituted or substituted $C_2$-$C_{17}$ heteroaryl group, a $C_5$-$C_{12}$ dienone group, or a combination thereof.

In some embodiments, the out-of-band absorbing monomer has the structure

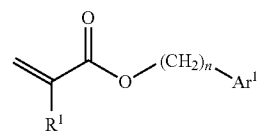

wherein $R^1$ is hydrogen or methyl; n is 0, 1, 2, 3, or 4; and $Ar^1$ is an unsubstituted or substituted $C_6$-$C_{18}$ aryl group, provided that the substituted $C_6$-$C_{18}$ aryl group is free of fluorine.

Specific examples of out-of-band absorbing monomers include

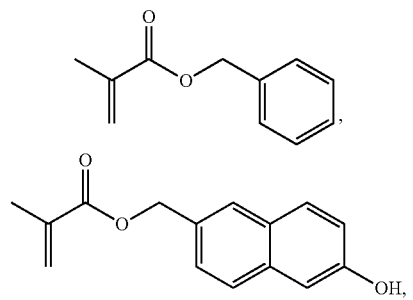

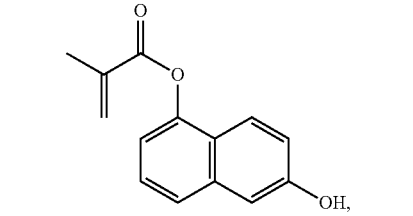

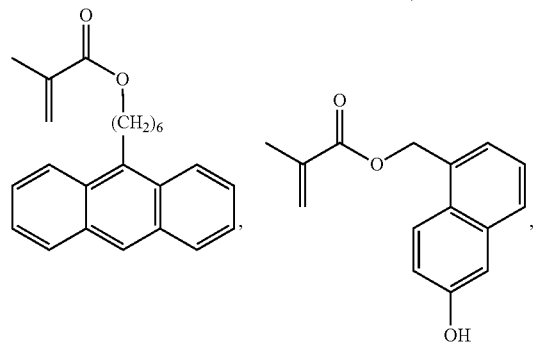

and combinations thereof.

The copolymer can comprise 20 to 60 mole percent of repeat units derived from the out-of-band absorbing monomer, based on 100 mole percent total repeat units in the copolymer. Within the range of 20 to 60 mole percent, the content of repeat units derived from the out-of-band absorbing monomer can be 30 to 50 mole percent.

In addition to repeat units derived from the out-of-band absorbing monomer, the copolymer comprises repeat units derived from a base-solubility-enhancing monomer. Base-solubility-enhancing monomers include (meth)acrylate esters of poly(ethylene oxide)s, (meth)acrylate esters of poly(propylene oxide)s, base-labile (meth)acrylate esters, (meth)acrylate esters substituted with a group having a $pK_a$ of 2 to 12, and combinations thereof.

(Meth)acrylate esters of poly(ethylene oxide)s and poly(propylene oxide)s can have the structure

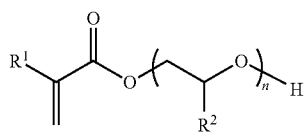

wherein $R^1$ is hydrogen (for acrylate) or methyl (for methacrylate), $R^2$ is hydrogen (for poly(ethylene oxide)) or methyl (for poly(propylene oxide)), and n is 3 to 50, specifically 5 to 30.

Base-labile (meth)acrylate esters include lactone-substituted monomers, such as, for example,

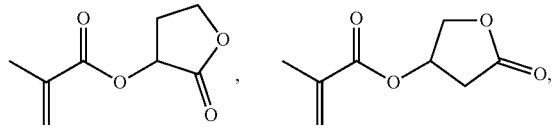

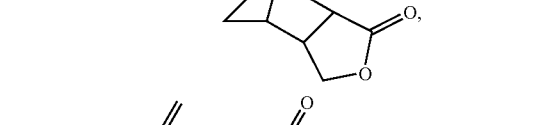

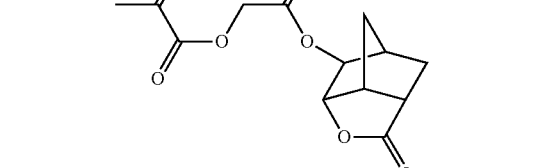

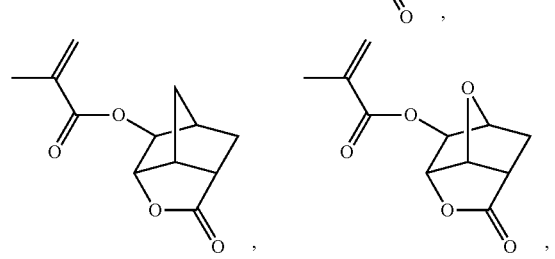

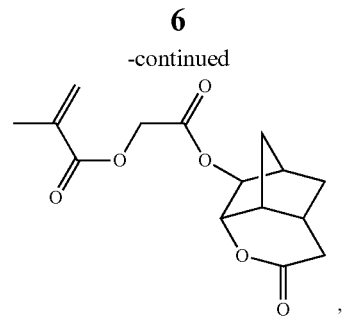

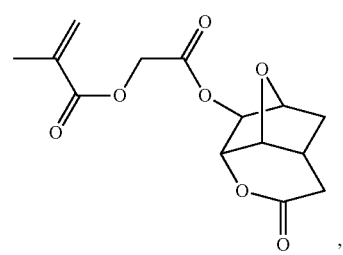

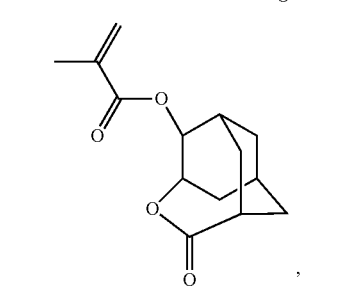

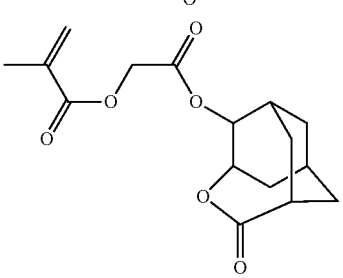

and combinations thereof.

(Meth)acrylate esters substituted with a group having a $pK_a$ of 2 to 12 include (meth)acrylate esters substituted with carboxylic acids, phenols, arylsulfonic acids, phthalimides, sulfonamides, sulfonimides, and alcohols. Those skilled in the art can readily determine if a particular species comprising one of these acidic functional groups has a $pK_a$ value in the range of 2 to 12. Specific examples of (meth)acrylate esters substituted with a group having a $pK_a$ of 2 to 12 include, for example,

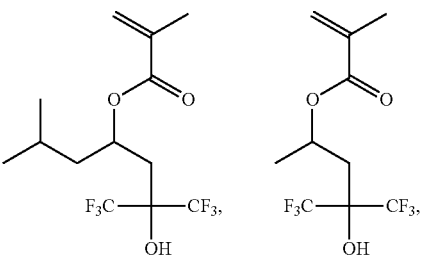

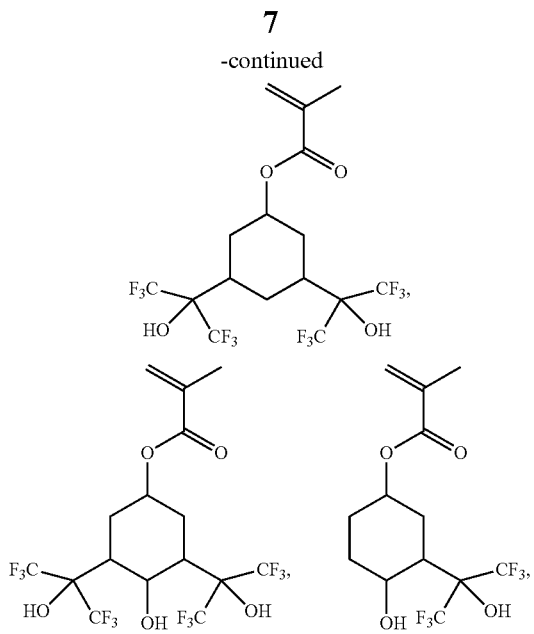
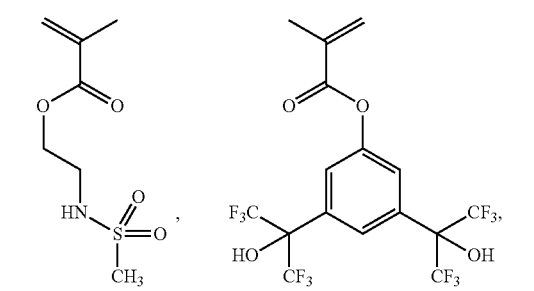
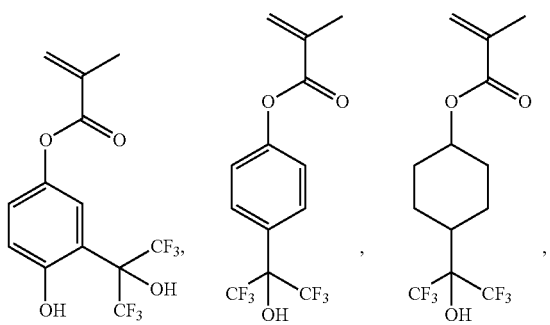
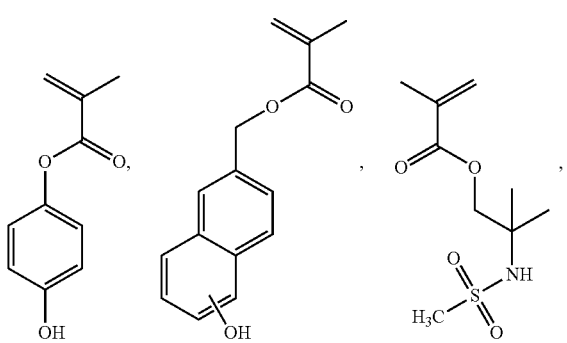

and combinations thereof.

In some embodiments, the base-solubility-enhancing monomer comprises a (meth)acrylate esters of poly(ethylene oxide), and a (meth)acrylate ester comprising a 1,1,1,3,3,3-hexafluoro-2-propyl group.

The copolymer can comprise 40 to 80 mole percent of repeat units derived from the base-solubility-enhancing monomer, based on 100 mole percent total repeat units in the copolymer. Within the range of 40 to 80 mole percent, the content of repeat units derived from the out-of-band absorbing monomer can be 50 to 70 mole percent. In a very specific embodiment, the copolymer comprises 30 to 50 mole percent of the (meth)acrylate ester of a poly(ethylene oxide), and 10 to 30 mole percent of the (meth)acrylate ester substituted with a 1,1,1,3,3,3-hexafluoro-2-propyl group.

In some embodiments, the copolymer consists of repeat units derived from the out-of-band absorbing monomer and the base-solubility-enhancing monomer.

The copolymer has an extinction coefficient "k" of 0.1 to 0.4 at 193 nanometer wavelength. Within this range, the extinction coefficient "k" can be 0.15 to 0.35 at 193 nanometer wavelength. A procedure for determining extinction coefficient "k" is described in the working examples.

There is no particular limitation on the molecular weight of the copolymer. Molecular weight characteristics can be determined by size exclusion chromatography using polystyrene standards and tetrahydrofuran solvent. In some embodiments, the copolymer has a number average molecular weight of 2,000 to 100,000 Daltons. Within this range, the number average molecular weight can be 3,000 to 60,000 Daltons, specifically 4,000 to 40,000 Daltons. Particularly when the copolymer is prepared using the RAFT methods described herein, it can have a narrow molecular weight distribution. The molecular weight distribution can be characterized by the dispersity, which is the ratio of the weight average molecular weight to the number average molecular weight. In some embodiments, the copolymer has a dispersity ($M_w/M_n$) of 1.05 to 1.2. Within this range, the dispersity can be 1.05 to 1.15. However, a narrow molecular weight distribution is not required for the copolymer to function as intended. For example, in some embodiments, the copolymer has a dispersity of 1.05 to 2.

In some embodiments, the copolymer is purified using a method selected from the group consisting of precipitation, filtration, solvent exchange, centrifugation, decantation (including multiple decantations), ion exchange, and combinations thereof.

In a very specific embodiment of the copolymer, the out-of-band absorbing monomer has the structure

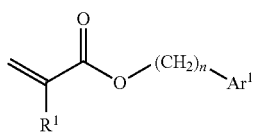

wherein $R^1$ is hydrogen or methyl, n is 0, 1, 2, 3, or 4, and $Ar^1$ is an unsubstituted or substituted $C_6$-$C_{18}$ aryl group that is free of fluorine; the base-solubility-enhancing monomer comprises a (meth)acrylate ester of a poly(ethylene oxide) and a (meth)acrylate ester substituted with a 1,1,1,3,3,3-hexafluoro-2-propyl group; the monomers comprise, based on the total moles of monomer, 30 to 50 mole percent of the out-of-band absorbing monomer, 30 to 50 mole percent of the (meth)acrylate ester of a poly(ethylene oxide), and 10 to 30 mole percent of the (meth)acrylate ester substituted with a 1,1,1,3,3,3-hexafluoro-2-propyl group; and the copolymer has a dispersity ($M_w/M_n$) of 1.05 to 1.2.

The copolymer is particularly useful for forming a topcoat layer for electron beam lithography or extreme ultraviolet lithography. The copolymer can constitute 50 to 100 weight percent of the topcoat layer. Optional components of the topcoat layer include hydrophobic additives to enhance physical separation of the topcoat layer from an underlying photoresist layer.

The topcoat layer can have a thickness of 5 to 50 nanometers, specifically 5 to 40 nanometers. Layer thickness can be controlled by varying the copolymer concentration in a solution for spin coating.

One embodiment is a method of forming a polymer layer, comprising spin-coating a copolymer solution comprising 0.1 to 3 weight percent of the copolymer (in any of its above-described variations) in a solvent selected from the group consisting of 2-methyl-2-butanol, 2-methyl-2-pentanol, combinations of 2-methyl-2-butanol and 2-methyl-2-pentanol, combinations of dipropylene glycol monomethyl ether and 2-methyl-2-butanol containing at least 90 weight percent 2-methyl-2-butanol, combinations of dipropylene glycol monomethyl ether and 2-methyl-2-pentanol containing at least 90 weight percent 2-methyl-2-pentanol, and combinations of dipropylene glycol monomethyl ether and 2-methyl-2-butanol and 2-methyl-2-pentanol containing at least 90 weight percent total of 2-methyl-2-butanol and 2-methyl-2-pentanol.

The invention further includes a layered article comprising: a substrate; a photoresist layer over the substrate; and a topcoat layer comprising the copolymer, in any of its above-described variations, over and in contact with the photoresist layer. In this embodiment, the layer article can, optionally, further comprise one or more additional layers between the substrate and the photoresist layer.

The invention further includes a method of forming an electronic device, comprising: (a) applying a photoresist onto a substrate; (b) applying a topcoat layer, in any of its above-described variations, onto the photoresist layer; (c) pattern-wise exposing the photoresist layer through the topcoat layer to activating radiation; and (d) developing the exposed photoresist layer to provide a resist relief image. The method can, optionally, further include (e) etching the resist relief pattern into the underlying substrate. In some embodiments, the activating radiation is electron beam or extreme ultraviolet radiation.

The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, having one or more layers and patterned features formed on a surface thereof. Optionally, the underlying base substrate material itself may be patterned, for example, when it is desired to form trenches in the base substrate material. Layers formed over the base substrate material may include, for example, one or more conductive layers such as layers of aluminum, copper, molybdenum, tantalum, titanium, tungsten, and alloys, nitrides or silicides of such metals, doped amorphous silicon or doped polysilicon, one or more dielectric layers such as layers of silicon oxide, silicon nitride, silicon oxynitride or metal oxides, semiconductor layers, such as single-crystal silicon, underlayers, antireflective layers such as a bottom antireflective layers, and combinations thereof. The layers can be formed by various techniques, for example, chemical vapor deposition (CVD) such as plasma-enhanced CVD, low-pressure CVD or epitaxial growth, physical vapor deposition (PVD) such as sputtering or evaporation, electroplating or spin-coating.

Any photoresist composition suitable for electron beam or extreme ultraviolet lithography can be used.

Applying the photoresist composition to the substrate can be accomplished by any suitable method, including spin coating, spray coating, dip coating, and doctor blading. In some embodiments, applying the layer of photoresist composition is accomplished by spin coating the photoresist in solvent using a coating track, in which the photoresist composition is dispensed on a spinning wafer. During dispensing, the wafer can be spun at a speed of up to 4,000 rotations per minute (rpm), specifically 500 to 3,000 rpm, and more specifically 1,000 to 2,500 rpm. The coated wafer is spun to remove solvent, and baked on a hot plate to remove residual solvent and free volume from the film to make it uniformly dense.

Pattern-wise exposure is then carried out using an exposure tool such as a stepper, in which the film is irradiated through a pattern mask and thereby is exposed pattern-wise. In some embodiments, the method uses advanced exposure tools generating activating radiation at wavelengths capable of high resolution including extreme-ultraviolet (EUV) or electron-beam (e-beam) radiation. The resolution of such exposure tools can be less than 30 nanometers.

Developing the exposed photoresist layer is then accomplished by treating the exposed layer and overlying topcoat layer with a suitable positive tone developer capable of uniformly dissolving the topcoat layer and selectively removing the exposed portions of the photoresist layer. In some embodiments, the positive tone developer is a metal-ion-free tetraalkylammonium hydroxide solution, such as, for example, aqueous 0.26 Normal tetramethylammonium hydroxide.

The photoresist composition can, when used in one or more such a pattern-forming processes, be used to fabricate electronic and optoelectronic devices such as memory devices, processor chips (including central processing units or CPUs), graphics chips, and other such devices.

Examples

Table 1 provides chemical structures and acronyms of monomers used in topcoat copolymer and photoresist copolymer synthesis.

TABLE 1

| | |
|---|---|
| PEGMA | Poly(ethylene glycol) methacrylate |

![PEGMA structure]

wherein n is, on average, about 9

| | |
|---|---|
| BzMA | Benzyl methacrylate |

![BzMA structure]

| | |
|---|---|
| HFACHOH | 4-(1,1,1,3,3,3-Hexafluoro-2-hydroxy-2-propyl)cyclohexyl methacrylate |

![HFACHOH structure]

Synthesis of Poly(PEGMA-co-BzMA-co-HFACHOH) statistical copolymer by the RAFT technique. A reaction scheme for the RAFT synthesis of poly(PEGMA-co-BzMA-co-HFACHOH) is presented in FIG. 1. PEGMA (4.75 gram, 0.01 mole), benzyl methacrylate (BzMA, 1.76 gram, 0.01 mole), HFACHOH (1.67 gram, 0.005 mole), 4-cyano-4-[(dodecylsufanylthiocarbonyl)sulfanyl]pentanoic acid (CDTPA, RAFT agent, 221.8 milligrams (91% pure), $5 \times 10^4$ mole), azoisobutyronitrile (AIBN, initiator, 8.2 milligrams, $5 \times 10^{-5}$ mole) and 1,4-dioxane (15 milliliters) were introduced in a 50 milliliter Schlenk flask equipped with a magnetic stirrer ($[M]_0$: $[mCTA]_0$: $[Init]_0$=50:1:0.1, [PEGMA]:[BzMA]:[HFACHOH]=2:2:1). The reaction mixture was purged with argon for 30 minutes in an ice bath to remove oxygen, and then heated at 70° C. The monomer conversion was calculated by $^1$H NMR and the polymer was recovered by double precipitation in hexane. The polymer was characterized by proton nuclear magnetic resonance spectroscopy ($^1$H NMR), ultraviolet-visible spectroscopy (UV-VIS) and size exclusion chromatography (SEC) using polystyrene standards and tetrahydrofuran solvent. SEC indicated a dispersity ($M_w/M_n$) of 1.12. Polymer characterization is summarized in Table 2.

TABLE 2

| | |
|---|---|
| Monomer 1 (M1) | PEGMA |
| Monomer 2 (M2) | BzMA |
| Monomer 3 (M3) | HFACHOH |
| M1 percent conversion (%) | 94.6 |
| M2 percent conversion (%) | 97.7 |
| M3 percent conversion (%) | 99.2 |
| theoretical molecular weight (Daltons) | 16,200 |
| M1 degree of polymerization | 19.1 |
| M2 degree of polymerization | 19.9 |
| M3 degree of polymerization | 9.6 |
| number average molecular weight, $^1$H NMR (Daltons) | 16,200 |
| Dispersity, SEC | 1.12 |

Figure 2:
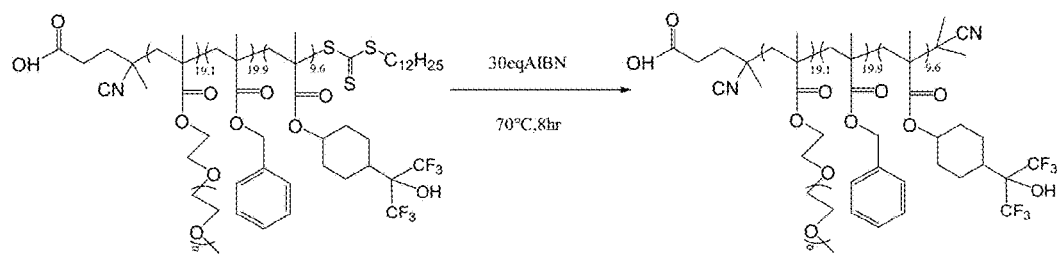
FIG. 2 is a reaction scheme for RAFT end group removal for poly(PEGMA-co-BzMA-co-HFACHOH).
Figure 3:
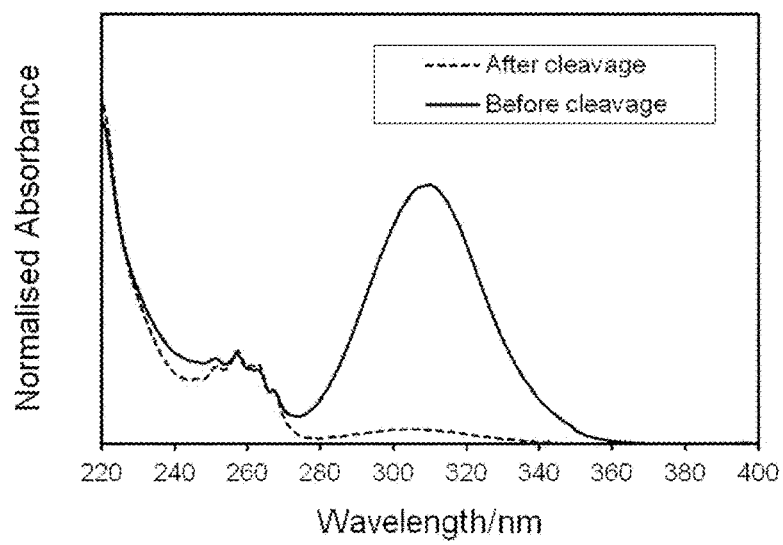
FIG. 3 provides normalized ultraviolet-visible spectra for poly(PEGMA-co-BzMA-co-HFACHOH) before and after RAFT end group cleavage (removal).
Figure 4:
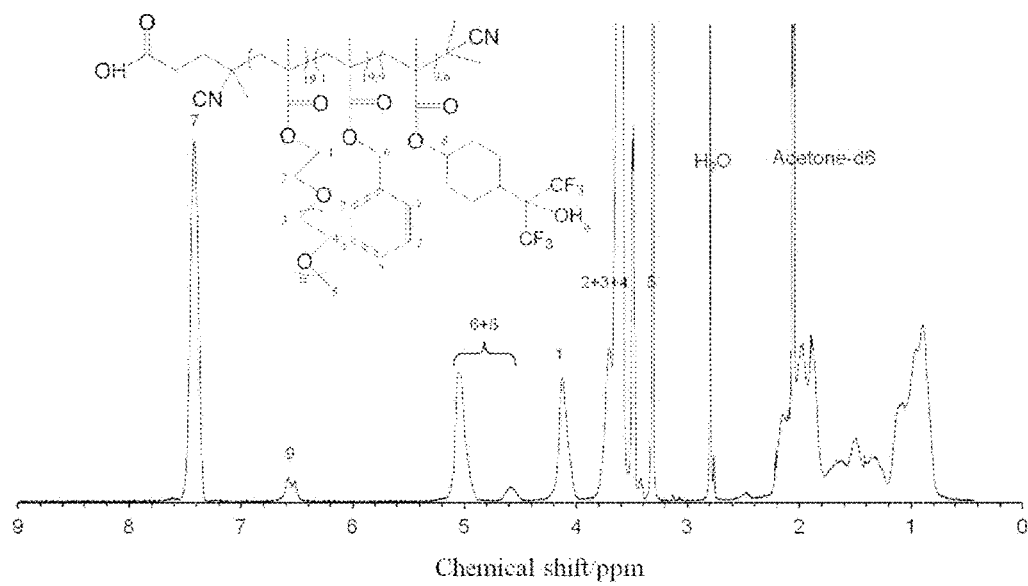
FIG. 4 is a $^1$H NMR spectrum of the topcoat polymer poly(PEGMA-co-BzMA-co-HFACHOH).

RAFT cleavage of Poly(PEGMA-co-BzMA-co-HFACHOH). A reaction scheme for end group removal from the RAFT polymer is presented in FIG. 2. The end-group cleavage of the statistical copolymer was carried out as follows. Poly (PEGMA-co-BzMA-co-HFACHOH) (3 grams, $1.85 \times 10^{-4}$ mole), AIBN (0.912 gram, $5.6 \times 10^{-3}$ mole, 30 equivalents) and 1,4-dioxane (25 milliliters) were introduced in a 100 mL Schlenk flask equipped with a magnetic stirrer. The reaction mixture was purged with argon for 30 minutes in an ice bath to remove oxygen, and then heated at 70° C. After 8 hours, the polymer was purified by dialysis in methanol and then removed the solvent. The polymer was characterized by $^1$H NMR, UV-VIS, and SEC. The $^1$H NMR spectrum is shown in FIG. 3, and the UV-VIS spectra of the copolymer before and after end group removal are presented in FIG. 4.

Thin Film Preparation

Figure 5A:
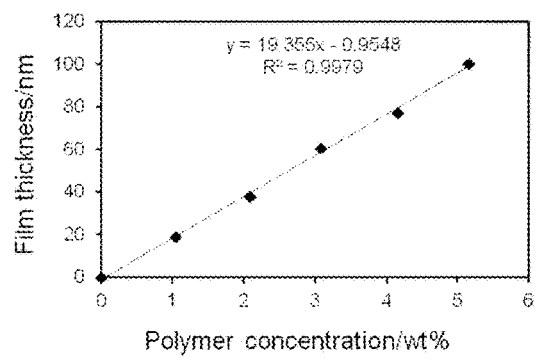
FIGS. 5A and 5B present plots of film thickness (nm) versus polymer concentration (weight percent (wt %)) for FIG. 5A a CBP-4 photoresist layer.
Figure 5B:
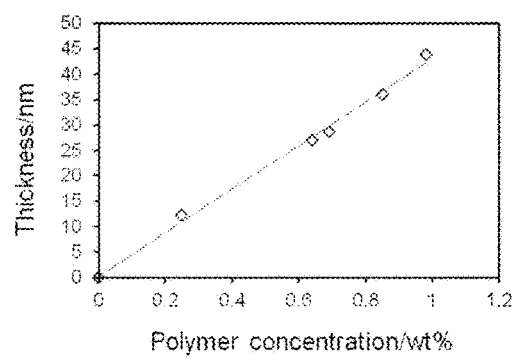

Determination of film thickness as a function of polymer concentration. The structure of photoresist polymer CBP-4 is shown in Table 3. A series of photoresist solutions was prepared as with photoresist polymer CBP-4 solutions at target concentrations 1, 2, 3, 4, and 5 weight percent in ethyl lactate or propylene glycol monomethyl ether acetate (PGMEA) as solvent. A representative spin coating process was carried out as follows. First, a silicon wafer was rinsed with acetone and isopropanol. Then the silicon wafer was placed on a 100° C. hotplate for 10 minutes. Then the silicon wafer was further cleaned by $O_2$ plasma treatment. The photoresist solution was spin coated onto the silicon wafer at a speed of 3000 rotations per minute (rpm) for 60 seconds. Following coating of the photoresist solution onto the wafer, the photoresist layer was dried by heating at 100° C. for 90 seconds to remove the solvent until the photoresist layer was tack free. Film thickness was measured on a SCI Filmtek 4000 spectroscopic reflectometer. The linear curve of film thickness versus polymer concentration is presented in FIG. 5a. According to the curve, 2.5 to 3 weight percent was used as final polymer concentration to achieve the desired photoresist layer thickness of about 50 nanometers.

TABLE 3

| Photoresist Polymer | |
|---|---|
| CBP-4 | ![Structure of CBP-4 with block ratios 32, 54, 9.2, 4.7 and pendant groups including phenyl, lactone, bis-CF3 cyclohexyl hydroxyl, and SO3⁻ ⁺SPh3] |

Thickness change of photoresist layer caused by different topcoat solvents. The purpose of this step was selection of a topcoat solvent. Generally, the topcoat solvent should not dissolve the photoresist layer. Otherwise, the solvent will partially dissolve the resist surface during the topcoat spin coating process, forming an intermixed layer. An effective method for evaluating the solvent compatibility between resist and topcoat is to measure the thickness change of the resist by exposing different topcoat solvents to the resist film A typical process was as follows. First, the photoresist solution was spin coated onto the silicon wafer. After the post-application bake, the thickness of the photoresist layer was measured. Then different solvents were applied by spin coating over photoresist layer. After another post-application bake, the film thickness was measured. Solvent properties are summarized in Table 4, where "TMAH" stands for tetramethylammonium hydroxide. The thickness change caused by different solvents is presented in Table 5, where "Di(propylene glycol) monomethyl ether+2-Methyl-2-butanol" refers to an 11:89 weight ratio of di(propylene glycol) monomethyl ether to 2-methyl-2-butanol.

TABLE 4

| Solvent | Topcoat Polymer Dissolution | Boiling point (° C.) |
| --- | --- | --- |
| Acetone | ✓ | 56 |
| Ethanol | ✓ | 78.1 |
| Methanol | ✓ | 64.7 |
| Tetrahydrofuran | ✓ | 66 |
| 2.38% TMAH | ✓ | — |
| Water | ✓ | 100 |
| Isobutanol | ✓ | 107.9 |
| 2-Methyl-2-butanol | ✓ | 102 |
| 2-Methyl-4-pentanol | ✓ | 131.6 |
| Anisole | ✓ | 154 |
| Di(propylene glycol) monomethyl ether | ✓ | 190 |

TABLE 5

| Solvent | Photoresist layer thickness before solvent application (nm) | Photoresist layer thickness after solvent application (nm) |
| --- | --- | --- |
| 2-Methyl-2-butanol | 48.1 ± 0.5 | 47.3 ± 0.4 |
| 2-Methyl-4-pentanol | 47.5 ± 3.7 | 46.7 ± 0.3 |
| Anisole | 47.5 ± 0.8 | 6.7 ± 2.5 |
| Di(propylene glycol) monomethyl ether | 47.1 ± 0.2 | 9.1 ± 1.8 |
| Di(propylene glycol) monomethyl ether + 2-Methyl-2-butanol | 46.6 ± 0.5 | 45.2 ± 1.2 |

Intermixing Test

A typical process for the intermixing test was carried out as follows. First, the photoresist solution was spin coated on the silicon wafer to form a 50 nanometer layer. After the post-application bake, the thickness of the photoresist layer was measured. Then the topcoat solution (poly(PEGMA-co-BzMA-co-HFACHOH) in 2-methyl-2-butanol) was spin coated over the photoresist layer. After the post-application bake, the total layer thickness was measured. The "dark loss" was measured after dissolving the topcoat layer in developer solution (2.38 weight percent TMAH solution) followed by rinsing with deionized water. The "dark loss" is the difference between the photoresist layer thickness before and after removing the topcoat and is called dark loss because no exposure is involved in the measurement.

The results of the intermixing test are shown Table 6. Coating of Poly(PEGMA-co-BzMA-co-HFACHOH)/2-methyl-2-butanol solution on a bare silicon substrate gave layer thicknesses of 10 nanometers (0.3 weight percent solution) or 27 nanometers (0.7 weight percent solution). The thicknesses of the photoresist layers were about 50 nanometers. After the topcoat was coated onto the photoresist layer, then the total layer thickness was about 60 nanometers (for the 0.3 weight percent topcoat solution) or about 80 nanometers (for the 0.7 weight percent solution). After removing the topcoat layer using 2.38% TMAH solution and rinsing with deionized water, the final thickness of the photoresist layer was similar to its original thickness. These results demonstrate that the topcoat layer described herein did not form a mixed layer with the photoresist layer and could be removed using developer solution.

TABLE 6

| Sample | Photoresist layer thickness (nm) | Total thickness of photoresist and topcoat layers (nm) | Thickness after developer solution treatment (nm) |
| --- | --- | --- | --- |
| Photoresist layer + 10 nm topcoat coated from ethyl lactate | 54.1 ± 0.5 | 64.6 ± 0.7 | 53.8 ± 1.0 |
| Photoresist layer + 30 nm topcoat coated from ethyl lactate | 55.1 ± 0.4 | 81.2 ± 0.3 | 53.1 ± 0.7 |
| Photoresist layer + 10 nm topcoat coated from PGMEA | 51.8 ± 0.4 | 62.0 ± 0.7 | 50.5 ± 0.5 |
| Photoresist layer + 30 nm topcoat coated from PGMEA | 51.1 ± 0.3 | 77.3 ± 0.5 | 48.6 ± 0.4 |

Measurement of Contact Angles

A typical procedure for preparing samples for contact angle measurement was as follows. A CBP-4 photoresist solution was spin coated onto a clean silicon wafer. No adhesion promoter coating was applied on the wafer prior to the photoresist layer. The topcoat solution was spin coated on the photoresist layer, forming a topcoat layer with a thickness of 10 or 30 nanometers. Contact angles were measured using a Dataphysics OCA20 contact-angle system at room temperature. Deionized water droplets (2 microliters) were dropped onto sample surfaces in order to conduct measurements of the wetting behavior.

Figure 6:
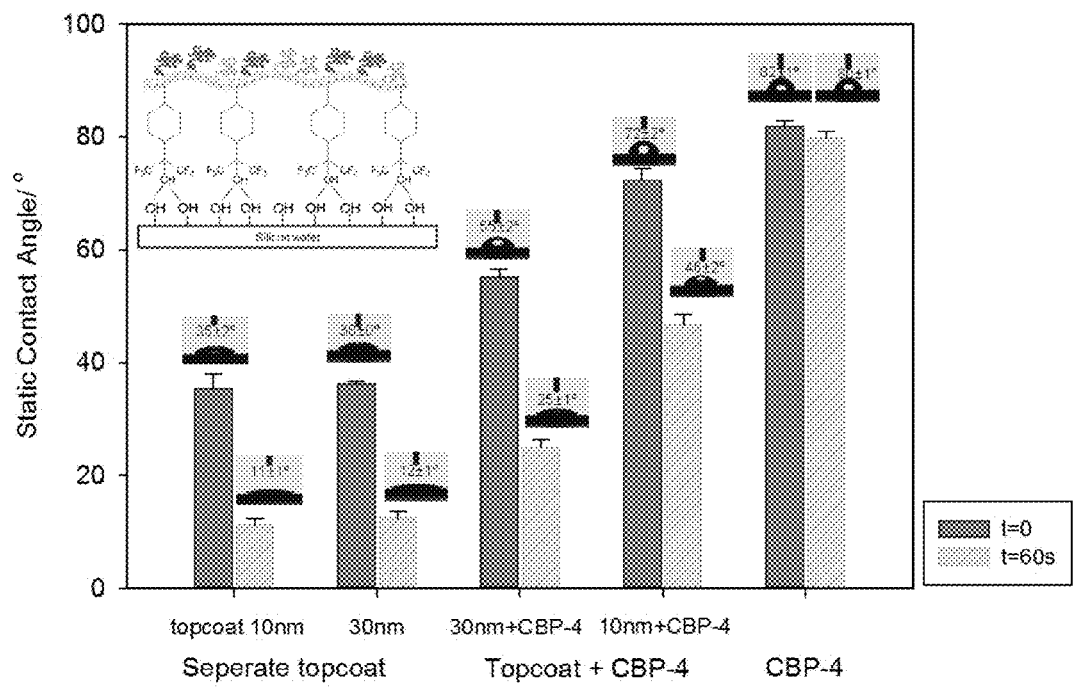
FIG. 6 is plot of contact angle (°) as a function of development time (1 or 60 seconds) for a 10 nanometer topcoat, a 30 nanometer topcoat, CBP-4+10 nm topcoat, CBP-4+30 nm topcoat, and CBP-4.

The results, presented in FIG. 6, show that the bare topcoat layer (10 or 30 nanometers) was quite hydrophilic. The deionized water contact angle was around 35° and the deionized water drop was spreading very quickly. After 60 seconds, the deionized water contact angle became about 11°. However, in the case of the topcoat coated on the photoresist layer, the water contact angle differed from that of the bare topcoat coated directly on the silicon wafer. For a topcoat with a thickness of 30 nanometers, the water contact angle (WCA) was 55° and became 25° after 60 seconds. For a topcoat layer with a thickness of 10 nanometers, the WCA was 72° and became 46° after 60 seconds. The WCA was 82° and stayed constant on the bare photoresist layer surface after 60 seconds. It is known that silicon readily oxidizes in air and is coated with a layer of silicon oxide which is a hydrophilic surface. While not wishing to be bound by any particular hypothesis, the inventors speculate that, shown in the schematic image in FIG. 6, the hydrophilic hydroxyl group hydrogen atoms on the wafer surface may hydrogen bond with the oxygen atoms of the hydroxyl groups of the HFACHOH repeat units. Consequently, the topcoat layer surface may tend to be more hydrophilic. However, when the topcoat layer is spin coated on the photoresist layer, more HFACHOH repeat units may move to surface because of the low surface energy during the spin coating process. This may be a reason that a topcoat layer coated on a photoresist layer tends to be more hydrophobic than a topcoat layer coated directly on a silicon substrate.

VUV VASE Ellipsometer Characterization

Figure 7:
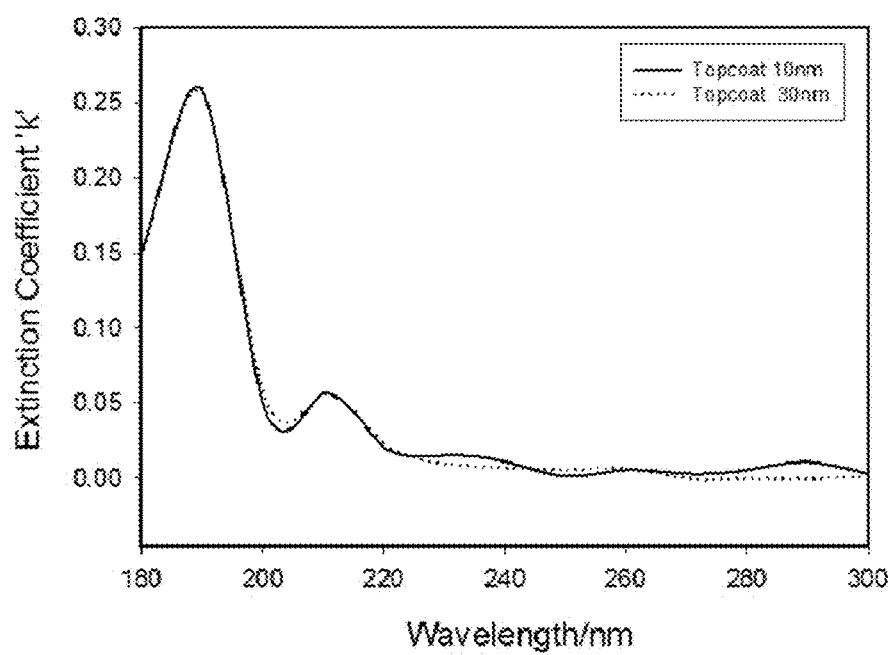
FIG. 7 is a plot of extinction coefficient versus wavelength (nm) for topcoats having 10 and 30 nanometer thicknesses.
Figure 8:
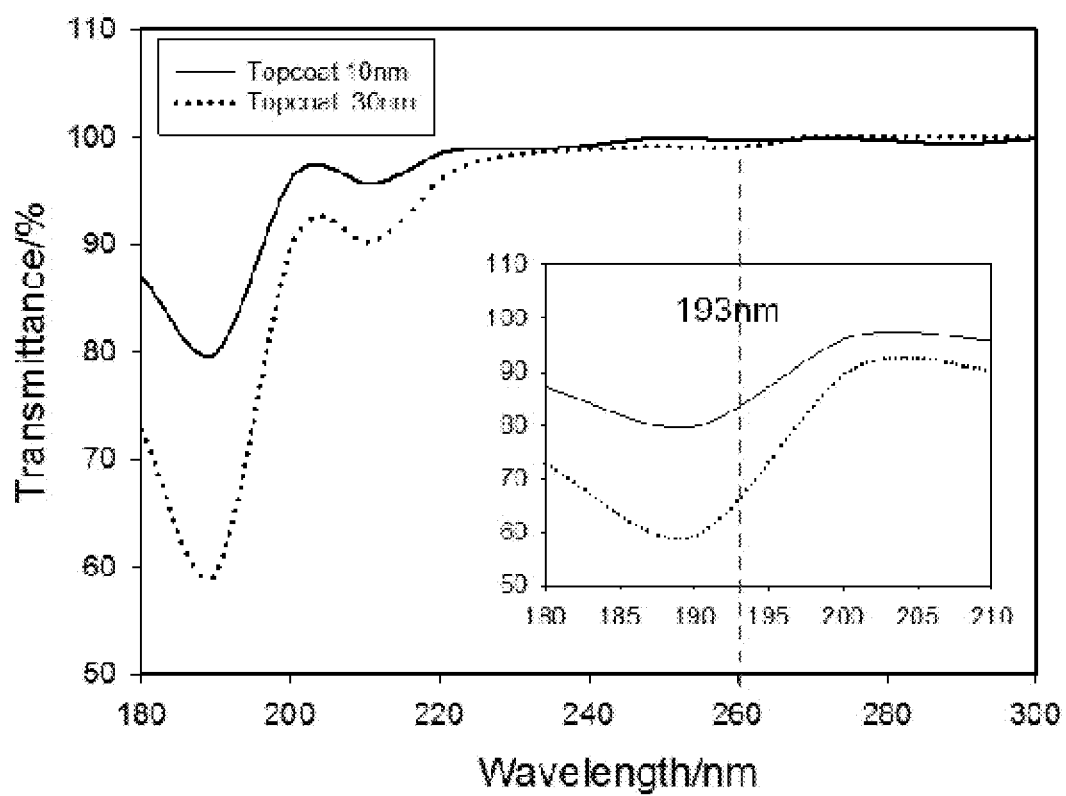
FIG. 8 is a plot of transmittance (%) versus wavelength (nm) for topcoats having 10 and 30 nanometer thicknesses.

In order to examine the blocking effect of the topcoat layer to the out-of-band light, the optical properties of the topcoat thin films were measured by VUV VASE ellipsometer. Optical constants, n and k, and film thicknesses were measured on a J. A. Woollam™ VUV VASE™ Spectroscopic Ellipsometer. The VUV VASE measurements were performed using a spectral range from 1.2 to 8.3 electronvolts (eV), corresponding to a wavelength range λ150-1000 nanometers, and angles of incidence of 65°-75°, by 5° as a step. The entire optical path was enclosed inside a dry nitrogen purge to eliminate absorption from ambient water vapor and oxygen. The modeling and fitting procedure in this study consisted of first determining the thickness and optical constants of transparent region of spectra from 300 to 1000 nanometers using a Cauchy layer and then using a point-by-point method to fit the curve ranging from 150 to 300 nm in order to obtain the optical constants extinction coefficient 'k' and refractive index 'n'. Optical properties of topcoat layers are summarized in Table 7 and presented in FIG. 7 (extinction coefficient as a function of wavelength and topcoat layer thickness) and FIG. 8 (percent transmittance as a function of wavelength and topcoat layer thickness). As shown in Table 7, and FIGS. 7 and 8, for topcoat layers with thicknesses of 13 and 30 nanometers, the extinction coefficient k is 0.213 and 0.215, respectively. The transmittance percentage at 193 nanometers was calculated to be 83.2% and 64%, respectively. The Absorption coefficients α were 13.9 and 14.0 μm$^{-1}$.

TABLE 7

| | Topcoat Layer Thickness (nm) | |
| --- | --- | --- |
| | 13.24 ± 0.03 | 30.82 ± 0.01 |
| extinction coefficient, k, at 193 nm | 0.213 | 0.215 |
| refractive index, n, at 193 nm | 1.742 | 1.720 |
| T (%) at 193 nm | 83.2 | 64.0 |
| Absorption coefficient α (μm$^{-1}$) | 13.9 | 14.0 |
| A/d Absorbance (μm$^{-1}$) | 6.03 | 6.08 |

Lithographic Performance

Samples for electron beam lithography (EBL) were prepared as follows. Photoresist polymer CBP-4 (25 milligrams) and triisopropanolamine (0.20 milligram, 20 mole percent relative to photoacid generating repeat units in the CBP-4 copolymer) were introduced in a 20 milliliter vial. Ethyl lactate (760 microliters, 786 milligrams) was added to make a solution with a CBP-4 polymer concentration of 3 weight percent. Topcoat polymer poly(PEGMA-co-BzMA-co-HFACHOH) (10 milligrams) was dissolved in 2-methyl-2-butanol (5 milliliters, 4.02 grams) to make a solution with a concentration of 0.25 weight percent.

A representative spin coating process was carried out as follows. First, the silicon wafer was rinsed with acetone and isopropanol. Then the silicon wafer was placed on 100° C. hotplate for 10 minutes. Then the silicon wafer was further cleaned by O$_2$ plasma treatment. An adhesion promoter obtained as TI/HDMS prime from MicroChemicals was spin coated on the clean silicon wafer at a speed of 3000 rpm for 20 seconds, followed by baking on a 120° C. hotplate for 5 minutes to remove the solvent. The photoresist solution was spin coated on the primer layer at a speed of 3000 rpm for 60 seconds. After coating of the photoresist solution onto the wafer, it was dried by heating at 100° C. for 90 seconds to remove the solvent until the photoresist layer was tack free. Then topcoat solution was spin coated over the photoresist layer at a speed of 3000 rpm for 60 seconds. For the post-application bake step, the coated wafer was placed on the 100° C. hotplate for 90 seconds to remove residual solvent.

The photoresist with topcoat layer was then patterned and exposed to activating radiation with the exposure energy typically ranging from about 10 to 100 μC/cm$^2$. Typically, the electron beam lithography technique was utilized as an exposure tool to generate patterns.

Following exposure, the photoresist with topcoat layer was baked at a temperature of 100° C. for 60 seconds. Thereafter, the sample was developed by treatment with an aqueous alkaline developer such as 0.26 N tetramethylammonium hydroxide (2.38 weight percent TMAH) for 20 seconds, followed by a water rinse for 20 seconds.

Electron beam lithographic analysis was conducted using a 7800 Field Emission Scanning Electron Microscope (FE-SEM) with a hot (Schottky) electron gun, which has a resolution (sample dependent) of 0.8 nm at 15 kV and 1.2 nm at 1 kV. It is equipped with a RAITH™ system for electron beam lithography.

Figure 9:
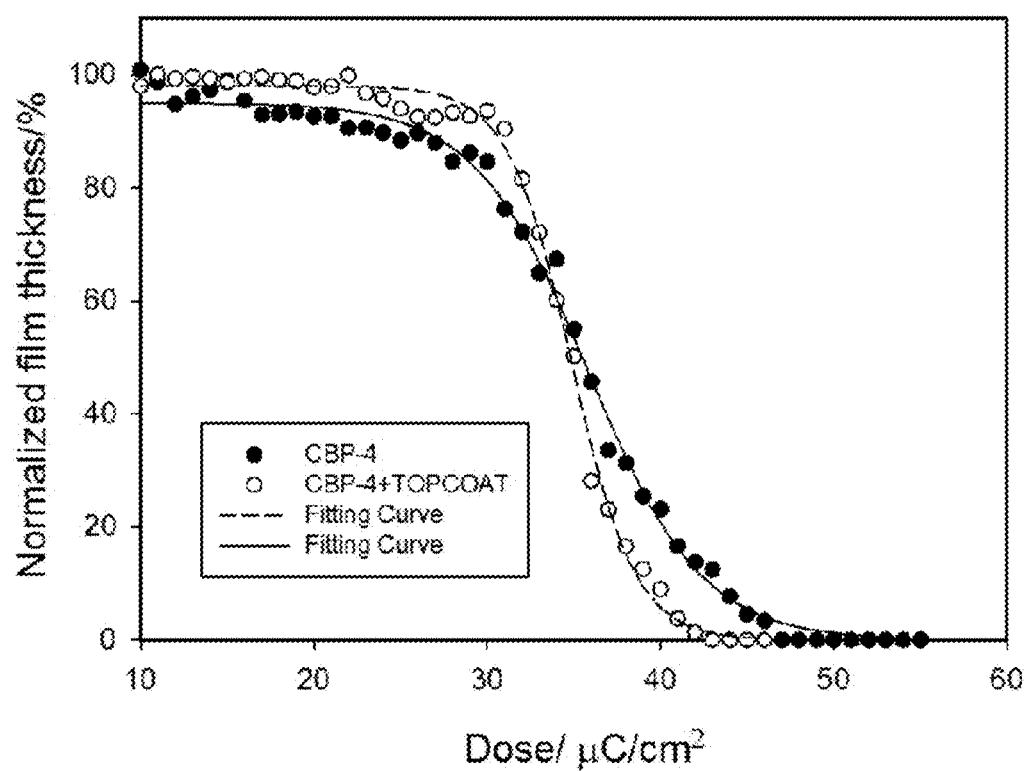
FIG. 9 is a plot of normalized film thickness (%) as a function of dose (microCoulomb/centimeter$^2$ ($\mu$C/cm$^2$)) for (a) CBP-4 photoresist, and (b) CBP-4 photoresist+10 nm topcoat.
Figure 10A:
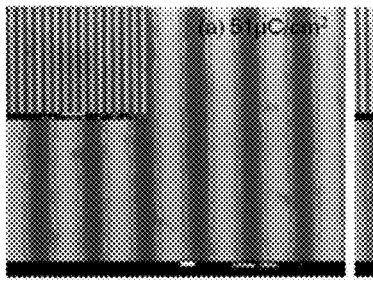
FIGS. 10A, 10B, 10C, 10D, 10E, and 10F consist of scanning electron micrographs (SEM) of line patterns for FIG. 10A photoresist CBP-4 at 51 $\mu$C/cm$^2$.
Figure 10B:
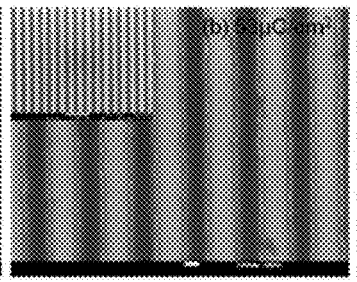
Figure 10C:
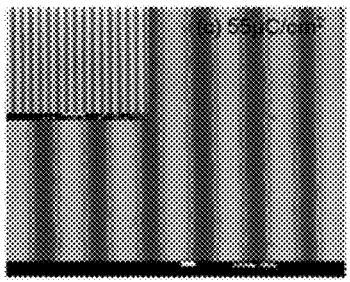
Figure 10D:
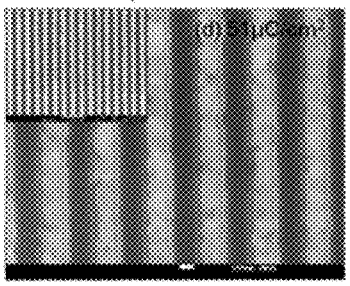
Figure 10E:
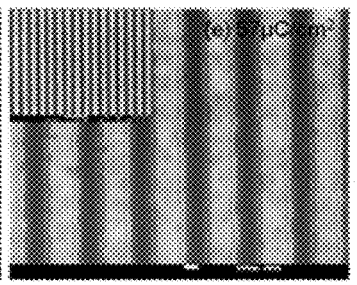
Figure 10F:
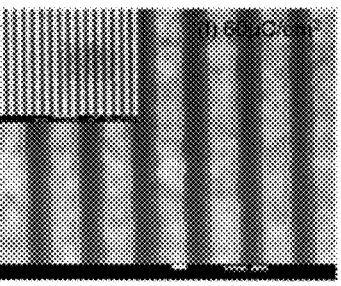

FIG. 9 shows contrast curves for CBP-4 photoresist layer, and CBP-4 photoresist layer plus 10 nanometer topcoat layer. It can be seen from the curves that the resist sensitivity did not change in the presence of topcoat layer. The doseto-clear values of the two samples were about 40 μC/cm². However, the slope is higher in the curve for CBP-4 photoresist layer plus 10 nanometer topcoat layer. Therefore, the contrast was improved with the addition of the topcoat layer. Scanning electron microscopy FIG. 10 presents scanning electron micrographs (SEM) of line patterns for (a) CBP-4 photoresist layer exposed at 51 μC/cm²; (b) CBP-4 photoresist layer exposed at 53 μC/cm²; (c) CBP-4 photoresist layer exposed at 55 μC/cm²; (d) CBP-4 photoresist layer+10 nm topcoat layer at exposed at 51 μC/cm²; (e) CBP-4 photoresist layer+10 nm topcoat layer at exposed at 57 μC/cm²; and (f) CBP-4 photoresist layer+10 nm topcoat layer at exposed at 60 μC/cm².

The invention claimed is:

1. A copolymer,
   wherein the copolymer comprises the polymerization product of monomers comprising:
   an out-of-band absorbing monomer comprising an unsubstituted or substituted $C_6$-$C_{18}$ aryl group that is free of fluorine, an unsubstituted or substituted $C_2$-$C_{17}$ heteroaryl group, a $C_5$-$C_{12}$ dienone group, or a combination thereof; and
   a base-solubility-enhancing monomer selected from the group consisting of (meth)acrylate esters of poly(ethylene oxide)s, (meth)acrylate esters of poly(propylene oxide)s, base-labile (meth)acrylate esters, (meth)acrylate esters substituted with a group having a $pK_a$ of 2 to 12, and combinations thereof;
   wherein the out-of-band absorbing monomer comprising an unsubstituted or substituted $C_6$-$C_{18}$ aryl group that is free of fluorine has the structure

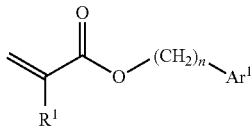

wherein
   $R^1$ is hydrogen or methyl,
   n is 0, 1, 2, 3, or 4, and
   $Ar^1$ is an unsubstituted or substituted $C_6$-$C_{18}$ aryl group that is free of fluorine;
   wherein a film cast from the copolymer has an extinction coefficient, k, of 0.1 to 0.5 at a wavelength in the range of 150 to 400 nanometers; and
   wherein the copolymer has a dispersity ($M_w/M_n$) of 1.05 to 1.2.

2. The copolymer of claim 1, wherein the base-solubility-enhancing monomer comprises a (meth)acrylate ester of a poly(ethylene oxide) and a (meth)acrylate ester substituted with a 1,1,1,3,3,3-hexafluoro-2-hydroxy-2-propyl group.

3. A method of forming a polymer layer, comprising spin-coating a polymer solution comprising 0.1 to 3 weight percent of the copolymer of claim 1 in a solvent selected from the group consisting of 2-methyl-2-butanol, 2-methyl-2-pentanol, combinations of 2-methyl-2-butanol and 2-methyl-2-pentanol, combinations of dipropylene glycol monomethyl ether and 2-methyl-2-butanol containing at least 90 weight percent 2-methyl-2-butanol, combinations of dipropylene glycol monomethyl ether and 2-methyl-2-pentanol containing at least 90 weight percent 2-methyl-2-pentanol, and combinations of dipropylene glycol monomethyl ether and 2-methyl-2-butanol and 2-methyl-2-pentanol containing at least 90 weight percent total of 2-methyl-2-butanol and 2-methyl-2-pentanol.

4. A layered article comprising:
   a substrate;
   a photoresist layer over the substrate; and
   a topcoat layer comprising the copolymer of claim 1, over and in contact with the photoresist layer.

5. A method of forming an electronic device, comprising:
   (a) applying a photoresist layer onto a substrate;
   (b) applying a topcoat layer comprising the copolymer of claim 1, onto the photoresist layer;
   (c) pattern-wise exposing the photoresist layer through the topcoat layer to activating radiation; and
   (d) developing the exposed photoresist layer to provide a resist relief image.

6. The method of claim 5, wherein the activating radiation comprises electron beam or extreme ultraviolet radiation.

7. A copolymer,
   wherein the copolymer comprises the polymerization product of monomers comprising:
   an out-of-band absorbing monomer having the structure

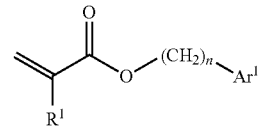

wherein $R^1$ is hydrogen or methyl, n is 0, 1, 2, 3, or 4, and $Ar^1$ is an unsubstituted or substituted $C_6$-$C_{18}$ aryl group that is free of fluorine; and
   a base-solubility-enhancing monomer comprising a (meth)acrylate ester of a poly(ethylene oxide) and a (meth)acrylate ester substituted with a 1,1,1,3,3,3-hexafluoro-2-hydroxy-2-propyl group;
   wherein the monomers comprise, based on the total moles of monomer,
   30 to 50 mole percent of the out-of-band absorbing monomer, 30 to 50 mole percent of the (meth)acrylate ester of a poly(ethylene oxide), and
   10 to 30 mole percent of the (meth)acrylate ester substituted with a 1,1,1,3,3,3-hexafluoro-2-hydroxy-2-propyl group;
   wherein the copolymer has a dispersity ($M_w/M_n$) of 1.05 to 1.2; and
   wherein a film cast from the copolymer has an extinction coefficient, k, of 0.1 to 0.5 at a wavelength in the range of 150 to 400 nanometers.

8. A copolymer,
   wherein the copolymer comprises the polymerization product of monomers comprising:
   an out-of-band absorbing monomer comprising an unsubstituted or substituted $C_6$-$C_{18}$ aryl group that is free of fluorine, an unsubstituted or substituted $C_2$-$C_{17}$ heteroaryl group, a $C_5$-$C_{12}$ dienone group, or a combination thereof; and
   a base-solubility-enhancing monomer selected from the group consisting of (meth)acrylate esters of poly(ethylene oxide)s, (meth)acrylate esters of poly(propylene oxide)s, base-labile (meth)acrylate esters, (meth)acrylate esters substituted with a group having a $pK_a$ of 2 to 12, and combinations thereof;

wherein the base-solubility-enhancing monomer comprises a (meth)acrylate ester of a poly(ethylene oxide) and a (meth)acrylate ester substituted with a 1,1,1,3,3,3-hexafluoro-2-hydroxy-2-propyl group;

wherein a film cast from the copolymer has an extinction coefficient, k, of 0.1 to 0.5 at a wavelength in the range of 150 to 400 nanometers; and wherein the copolymer has a dispersity ($M_w/M_n$) of 1.05 to 1.2.

\* \* \* \* \*